United States Patent
Han et al.

(10) Patent No.: US 10,371,828 B2
(45) Date of Patent: Aug. 6, 2019

(54) SCINTILLATOR USING SEMICONDUCTOR QUANTUM DOTS, MANUFACTURING METHOD THEREOF, AND DIGITAL IMAGE DIAGNOSTIC SYSTEM EMPLOYING THE SAME

(71) Applicant: Korea Electronics Technology Institute, Seongnam-si, Gyeonggi-do (KR)

(72) Inventors: Chuljong Han, Yongin-si (KR); Jeongno Lee, Yongin-si (KR); Minsuk Oh, Seoul (KR); Byungwook Yoo, Seoul (KR)

(73) Assignee: KOREA ELECTRONICS TECHNOLOGY INSTITUTE, Seongnam-si (KR)

( * ) Notice: Subject to any disclaimer, the term of this patent is extended or adjusted under 35 U.S.C. 154(b) by 13 days.

(21) Appl. No.: 15/992,060

(22) Filed: May 29, 2018

(65) Prior Publication Data

US 2018/0341028 A1    Nov. 29, 2018

(30) Foreign Application Priority Data

May 29, 2017   (KR) .................. 10-2017-0066148

(51) Int. Cl.
*G01T 1/20* (2006.01)
*G21K 4/00* (2006.01)
(Continued)

(52) U.S. Cl.
CPC .......... *G01T 1/2002* (2013.01); *A61B 6/4208* (2013.01); *G01T 1/1606* (2013.01);
(Continued)

(58) Field of Classification Search
CPC ....... G01T 1/2002; G01T 1/24; G01T 1/2018; A61B 6/4208; G21K 4/00
(Continued)

(56) References Cited

U.S. PATENT DOCUMENTS

| 9,698,311 B2 * | 7/2017 | Greco ................. G01N 33/588 |
| 2006/0226370 A1 * | 10/2006 | Gia ..................... C09K 11/7701 |
| | | 250/370.11 |

(Continued)

FOREIGN PATENT DOCUMENTS

| JP | 2005-009872 A | 1/2005 |
| JP | 2006-153874 A | 6/2006 |

(Continued)

OTHER PUBLICATIONS

Office Action of corresponding Korean Patent Application No. 10-2017-0066148—5 pages (dated Jul. 30, 2018).

*Primary Examiner* — David P Porta
*Assistant Examiner* — Gisselle M Gutierrez
(74) *Attorney, Agent, or Firm* — Knobbe Martens Olson & Bear LLP

(57) ABSTRACT

Disclosed are a scintillator using semiconductor quantum dots, a method of manufacturing the scintillator, and a digital image diagnostic system employing the scintillator. In one aspect, the scintillator includes a metallic reflection film made of a metal configured to transmit an X-ray and reflecting visible light and having a plurality of voids formed in a thickness direction. The scintillator also includes a polymer film formed inside the plurality of voids and being configured to include a plurality of columnar structures to convert the X-ray into the visible light. The scintillator further includes semiconductor quantum dots dispersed in the polymer film and having a decay time of tens of nanoseconds.

11 Claims, 16 Drawing Sheets

(51) Int. Cl.
*A61B 6/00* (2006.01)
*G01T 1/24* (2006.01)
*G01T 1/16* (2006.01)

(52) U.S. Cl.
CPC .............. *G01T 1/2018* (2013.01); *G01T 1/24* (2013.01); *G21K 4/00* (2013.01)

(58) Field of Classification Search
USPC ..................................................... 250/370.11
See application file for complete search history.

(56) References Cited

U.S. PATENT DOCUMENTS

2011/0122994 A1*  5/2011  Grubsky .................. G01T 1/20
378/62
2016/0231440 A1*  8/2016  Burke ....................... G01T 1/16

FOREIGN PATENT DOCUMENTS

| KR | 10-2011-0080363 A | 7/2011 |
| KR | 10-2014-0050305 | 4/2014 |
| KR | 10-2017-0029371 A | 3/2017 |

* cited by examiner

[FIG. 1]
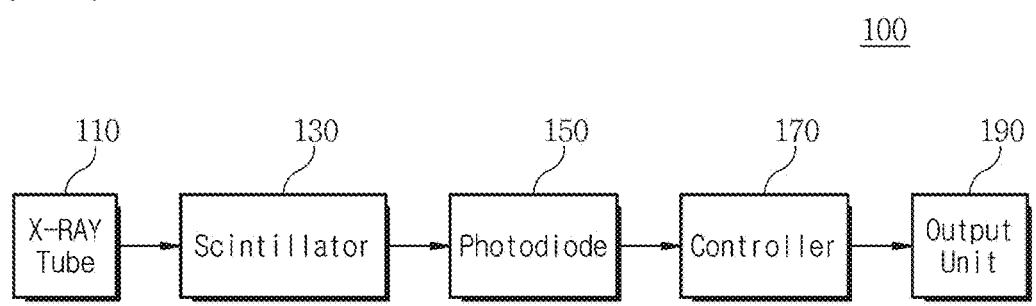
[FIG. 2]
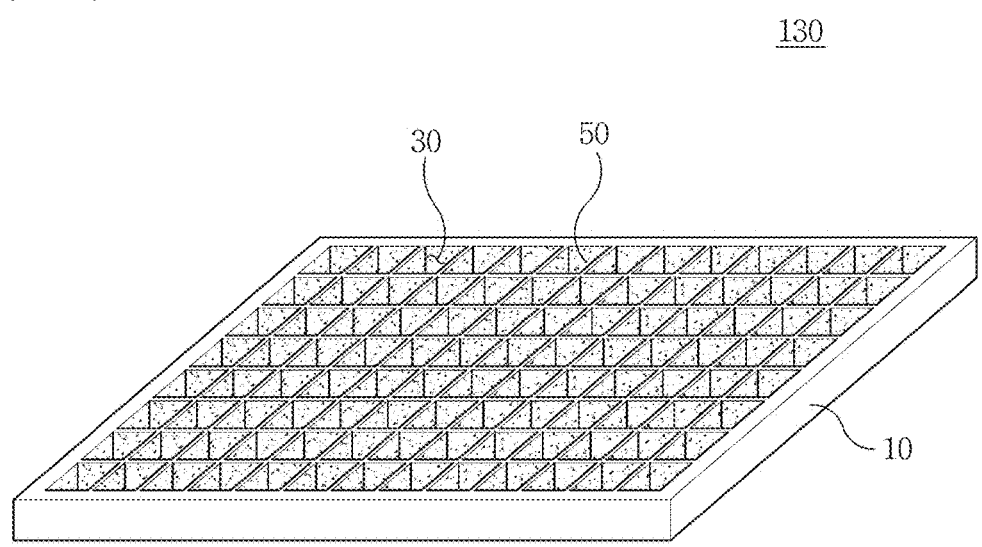

[FIG. 3]
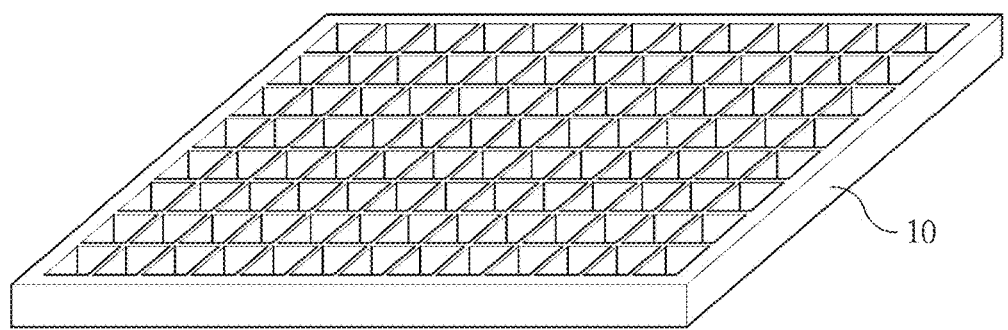
[FIG. 4]
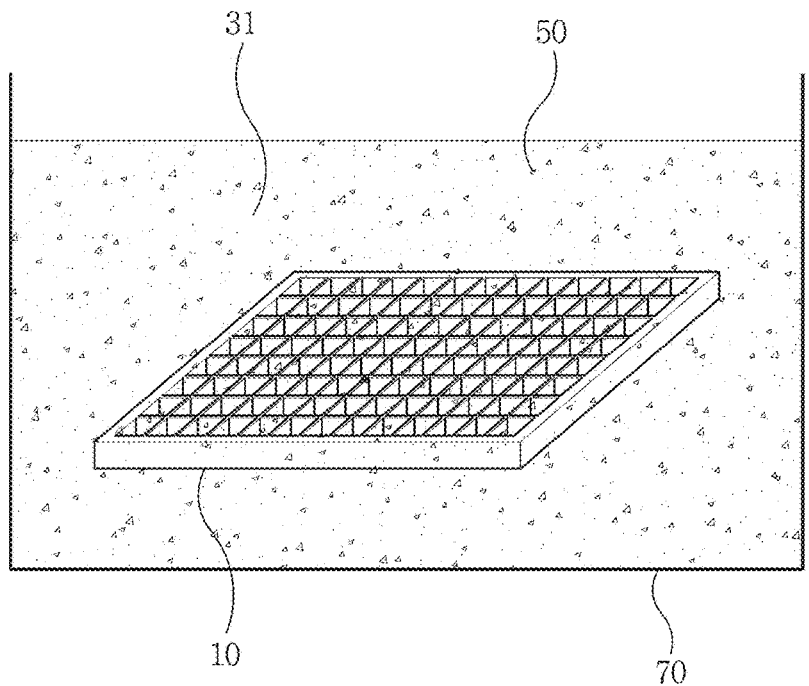

[FIG. 5]
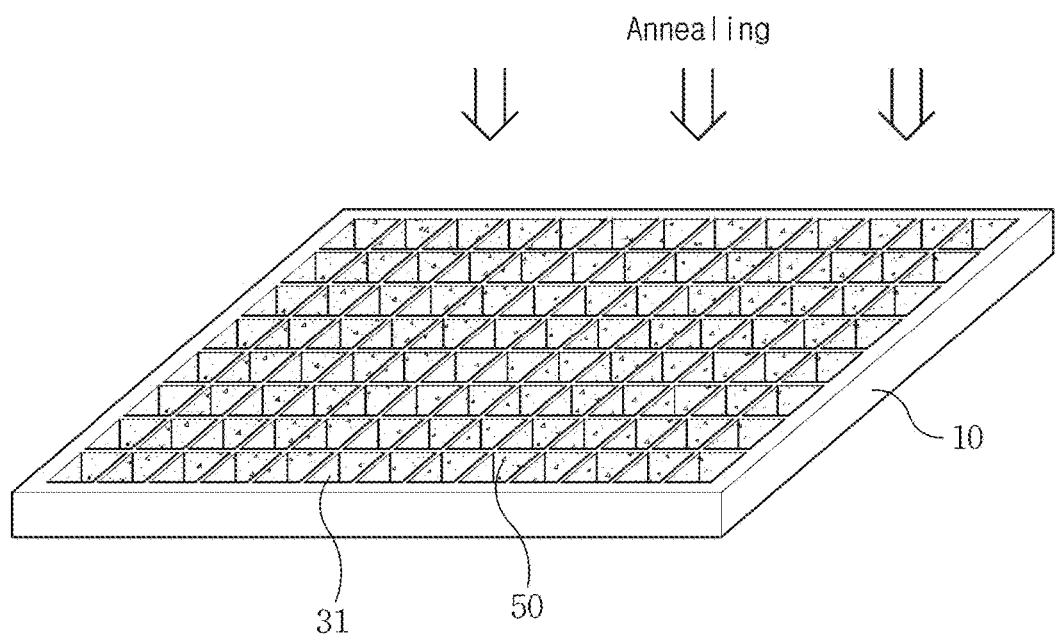

[FIG. 6]
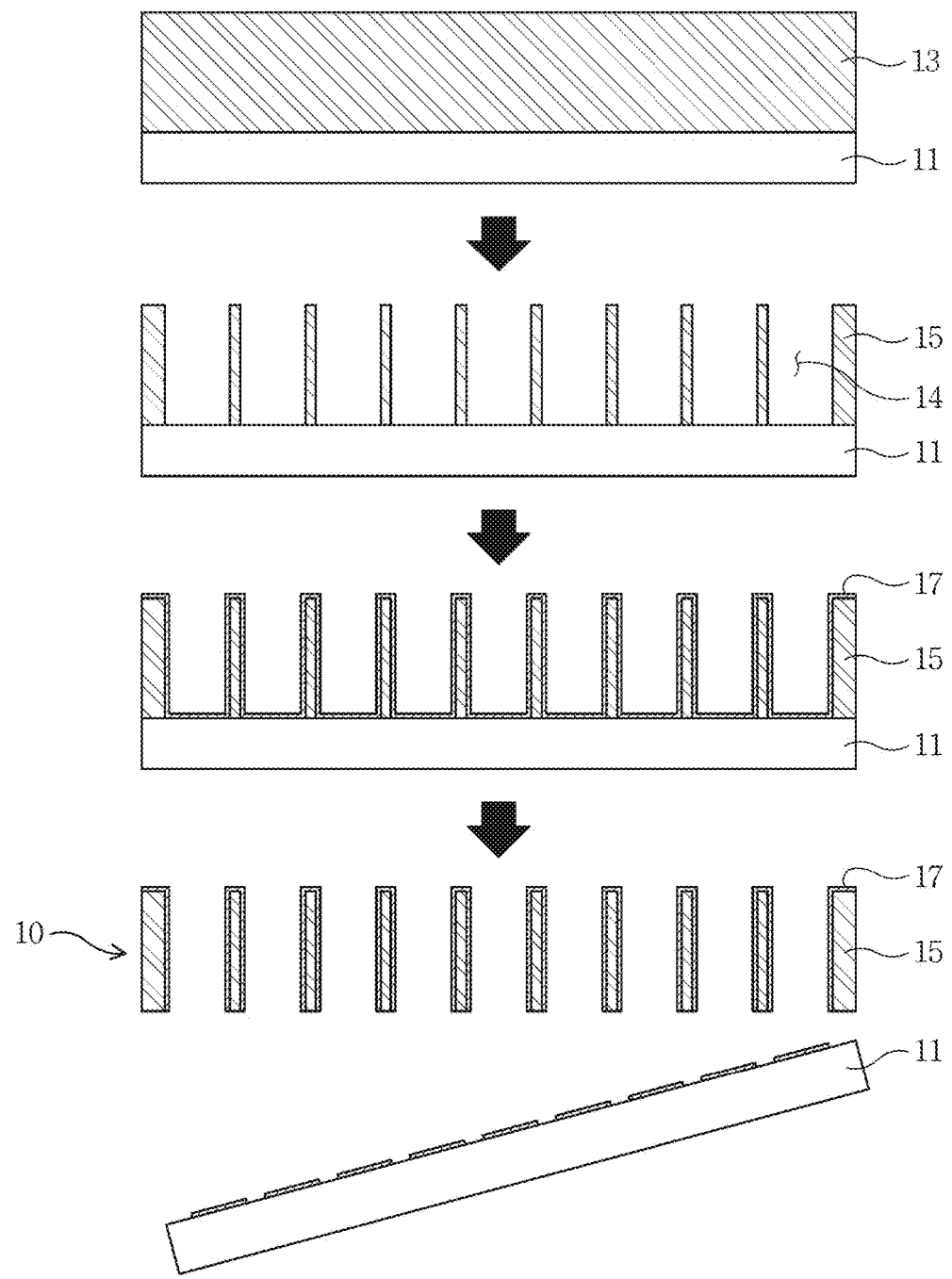

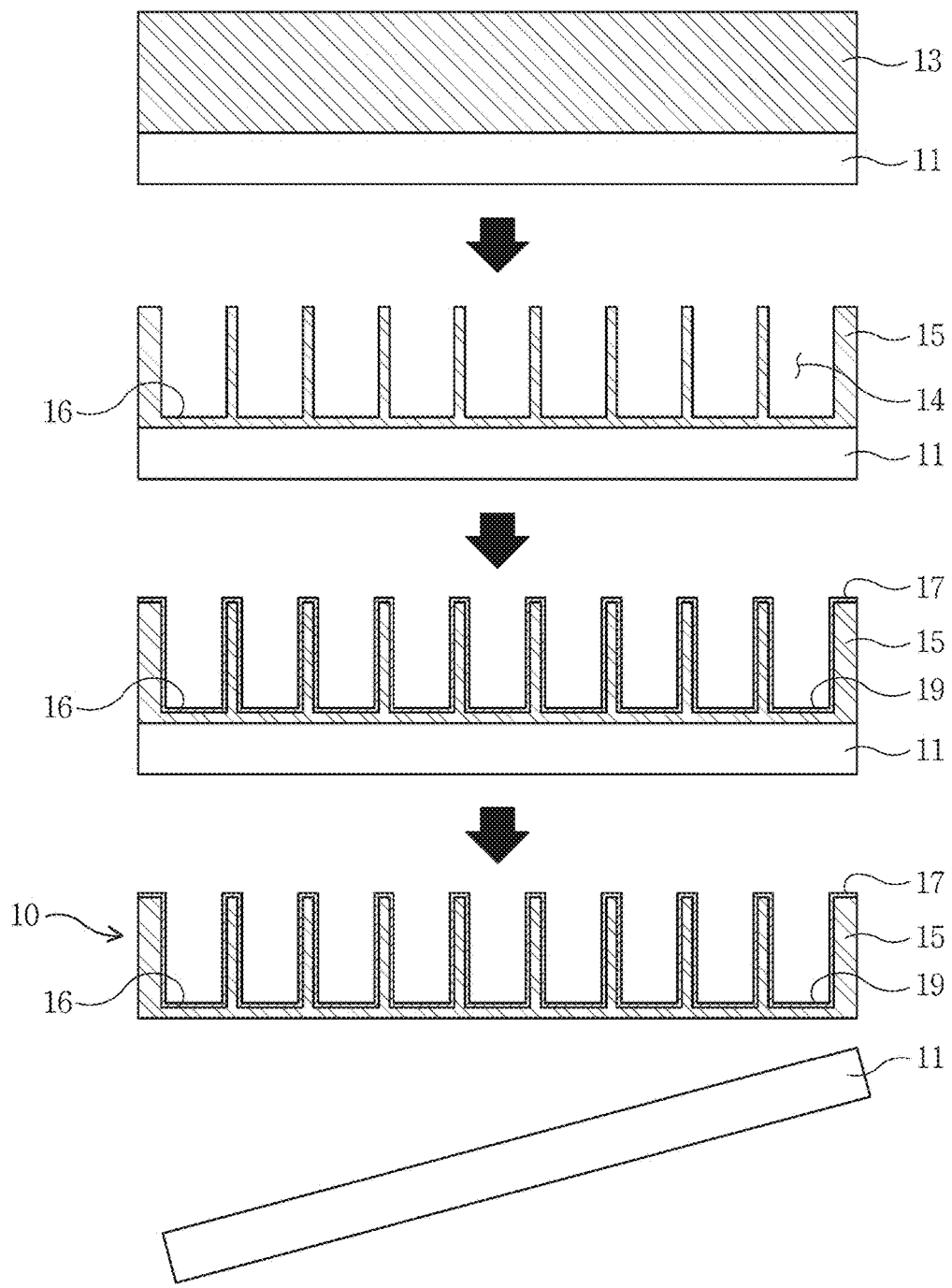
[FIG. 7]

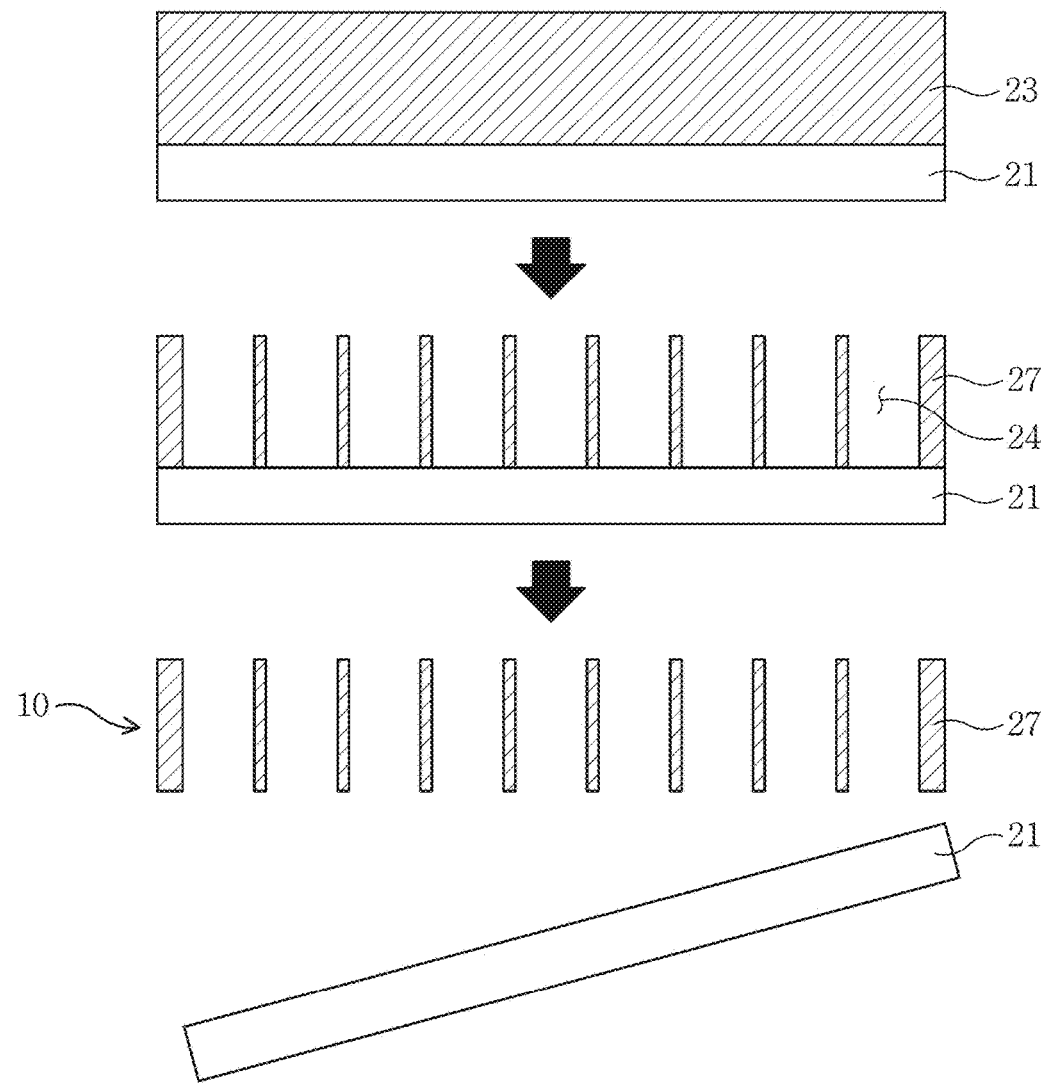
[FIG. 8]

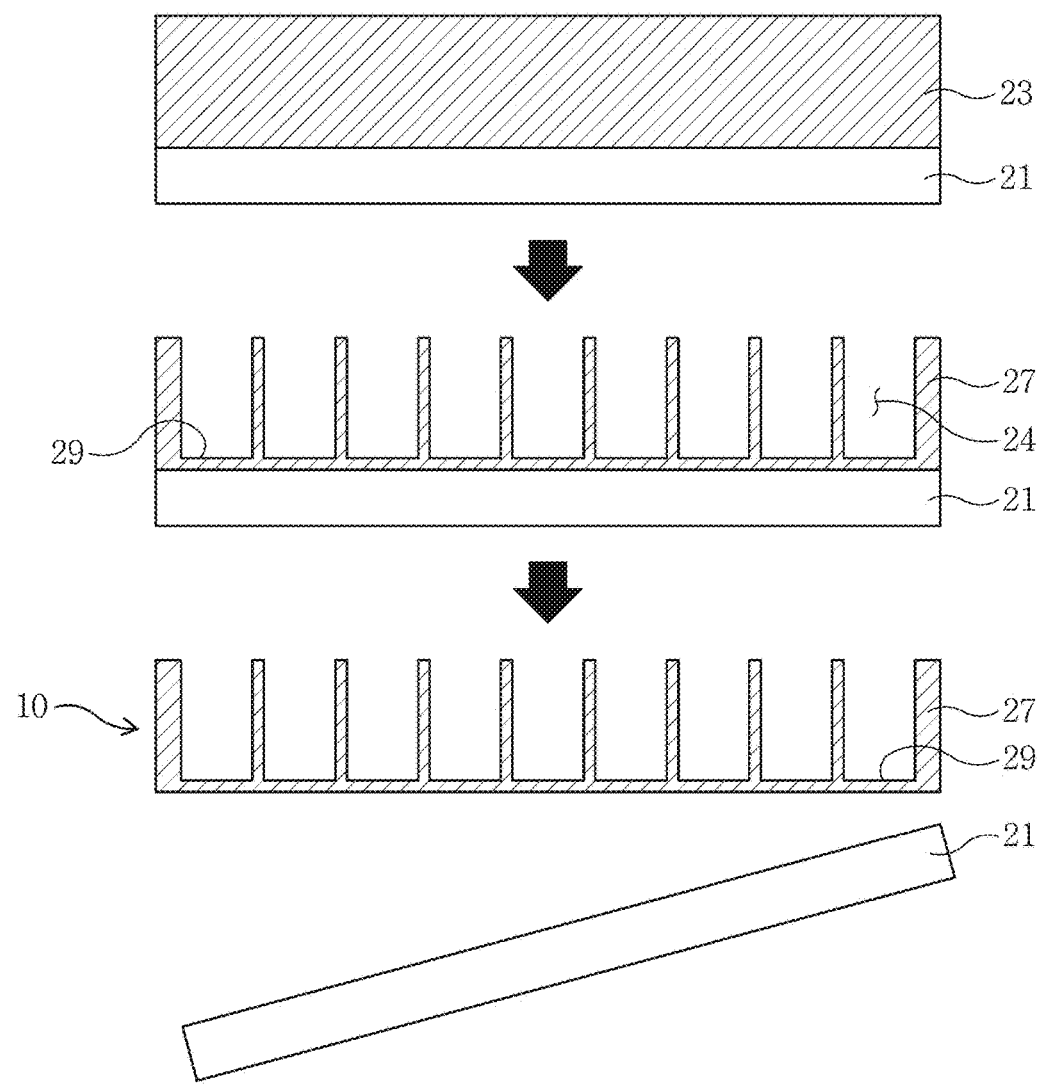
[FIG. 9]

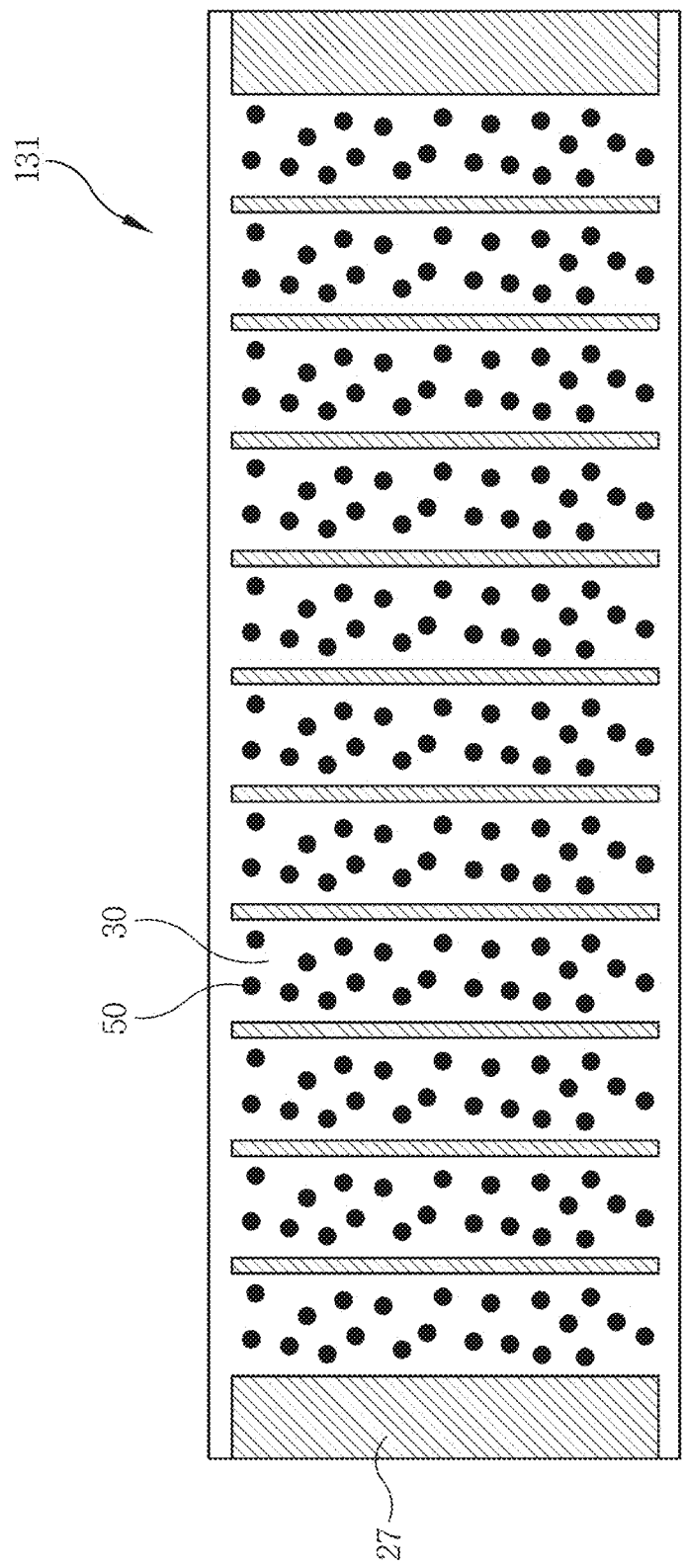

[FIG. 11]
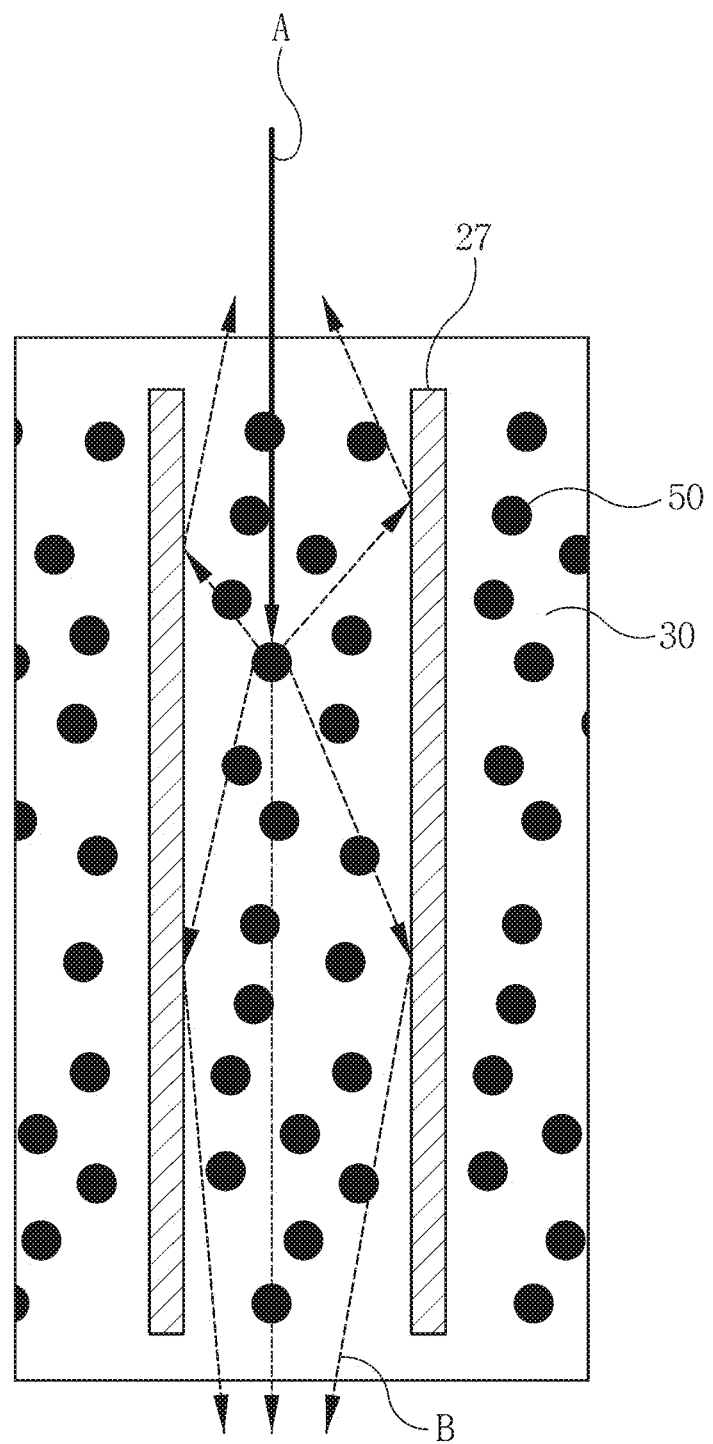

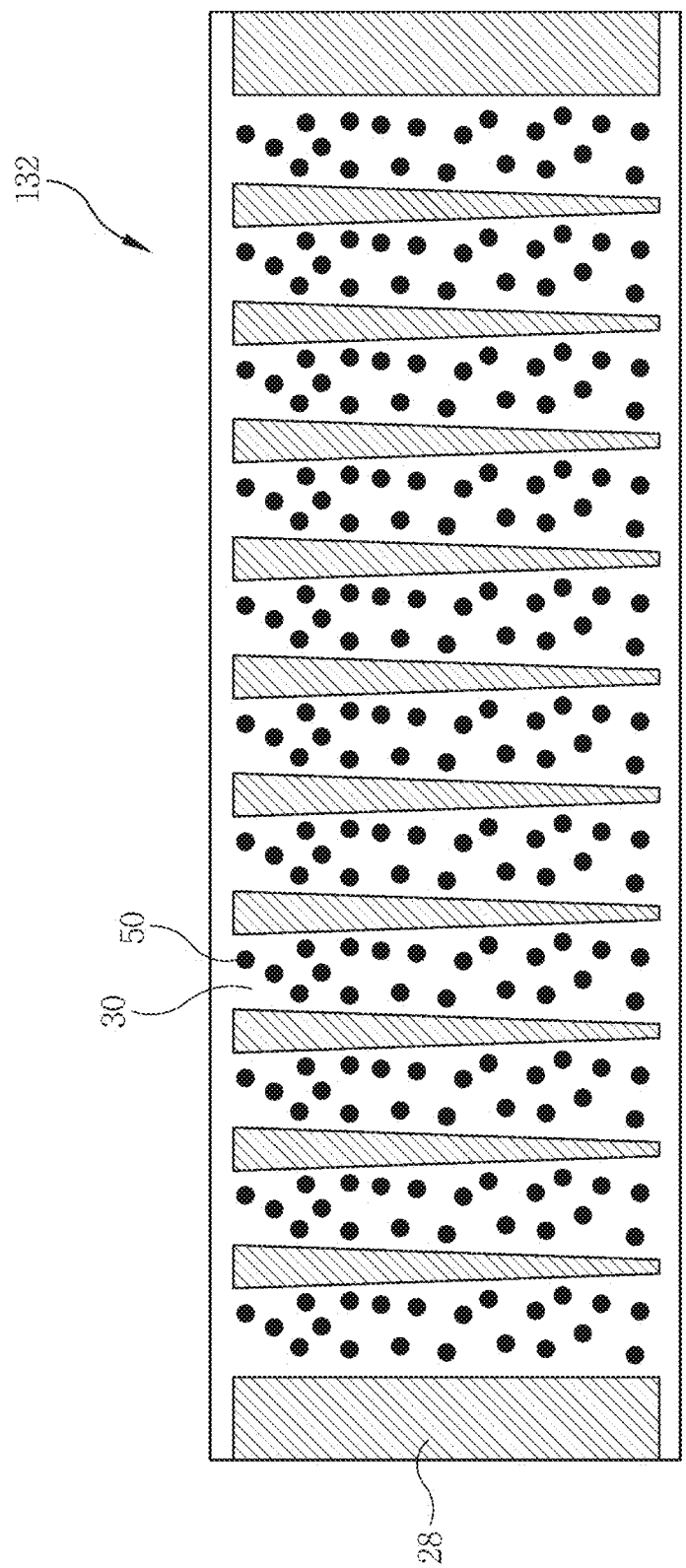
[FIG. 12]

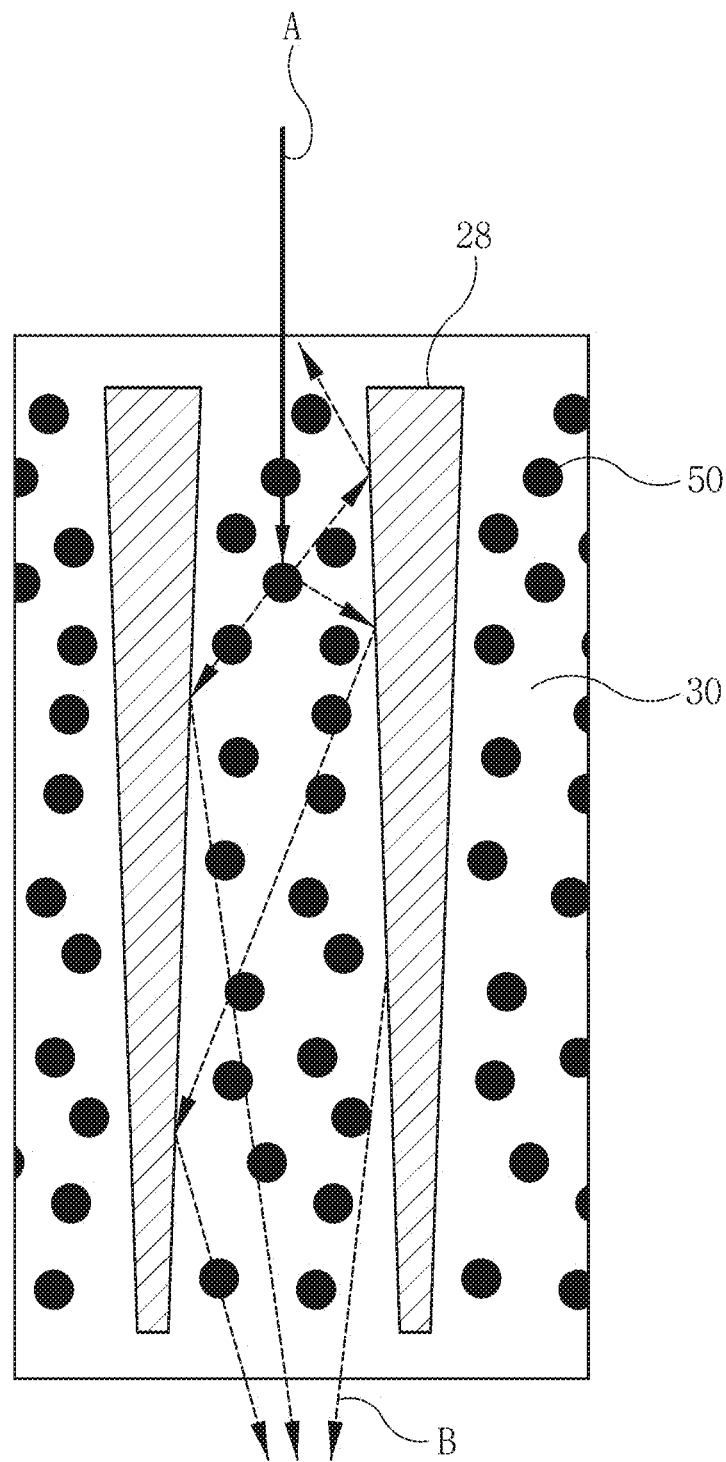
[FIG. 13]

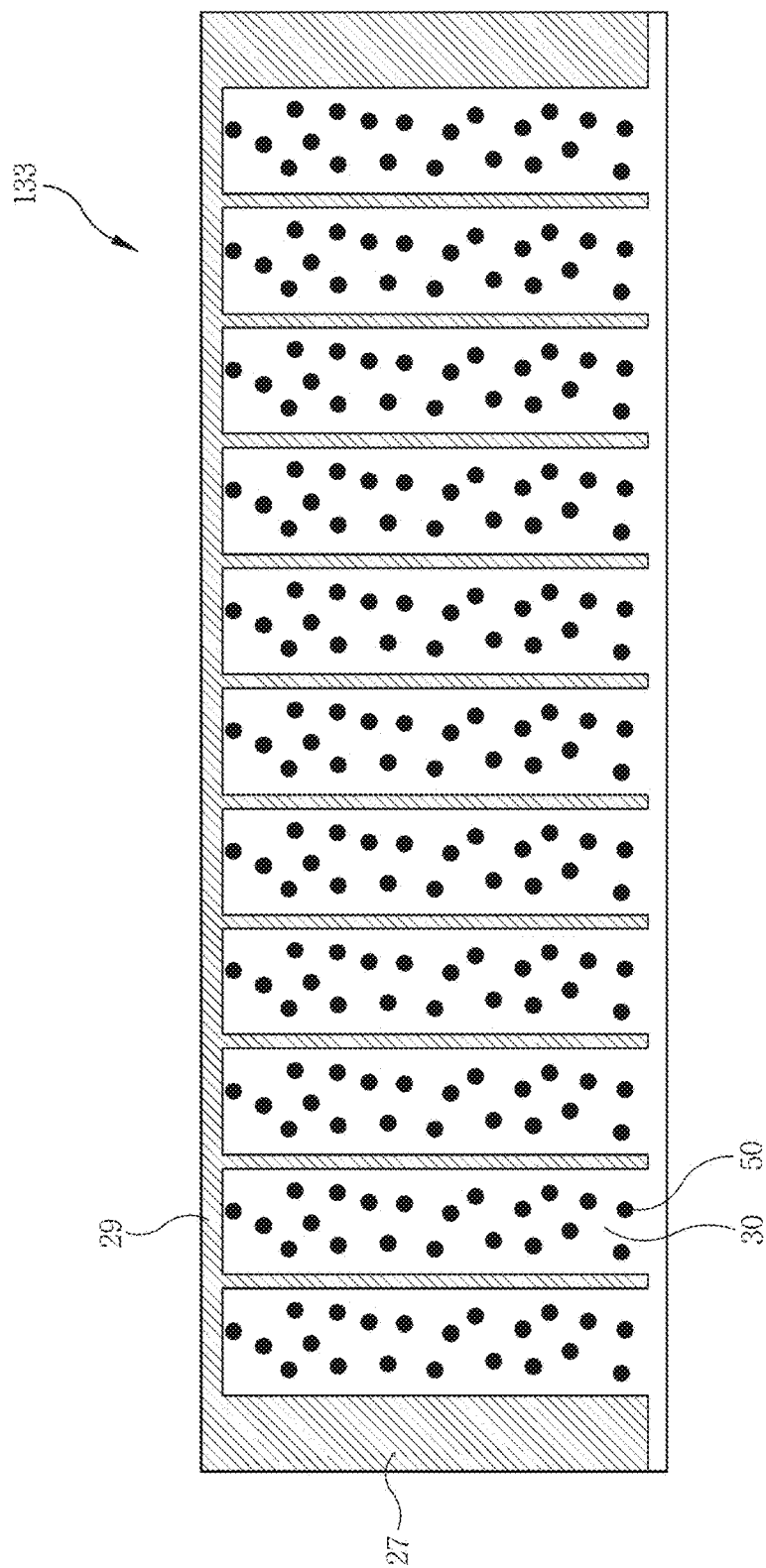
[FIG. 14]

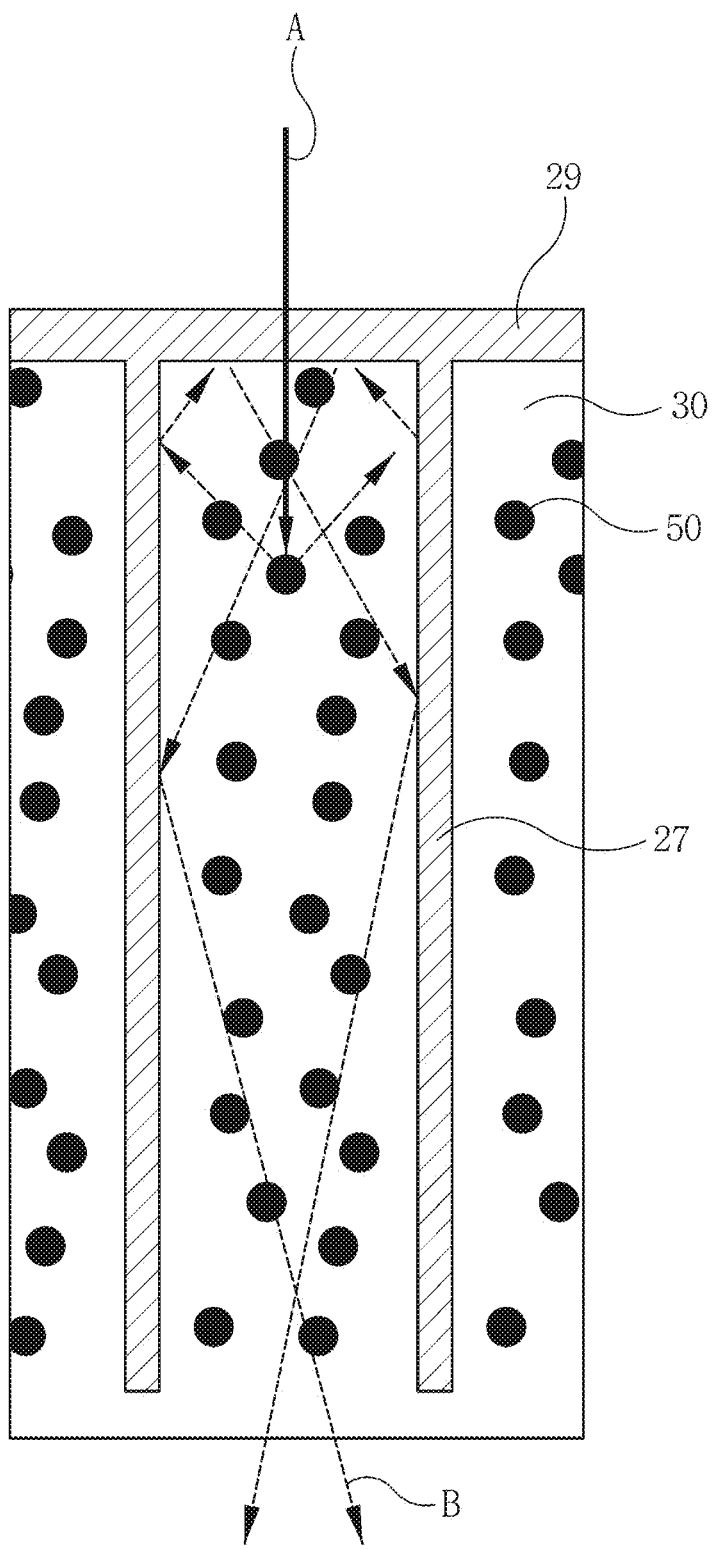
[FIG. 15]

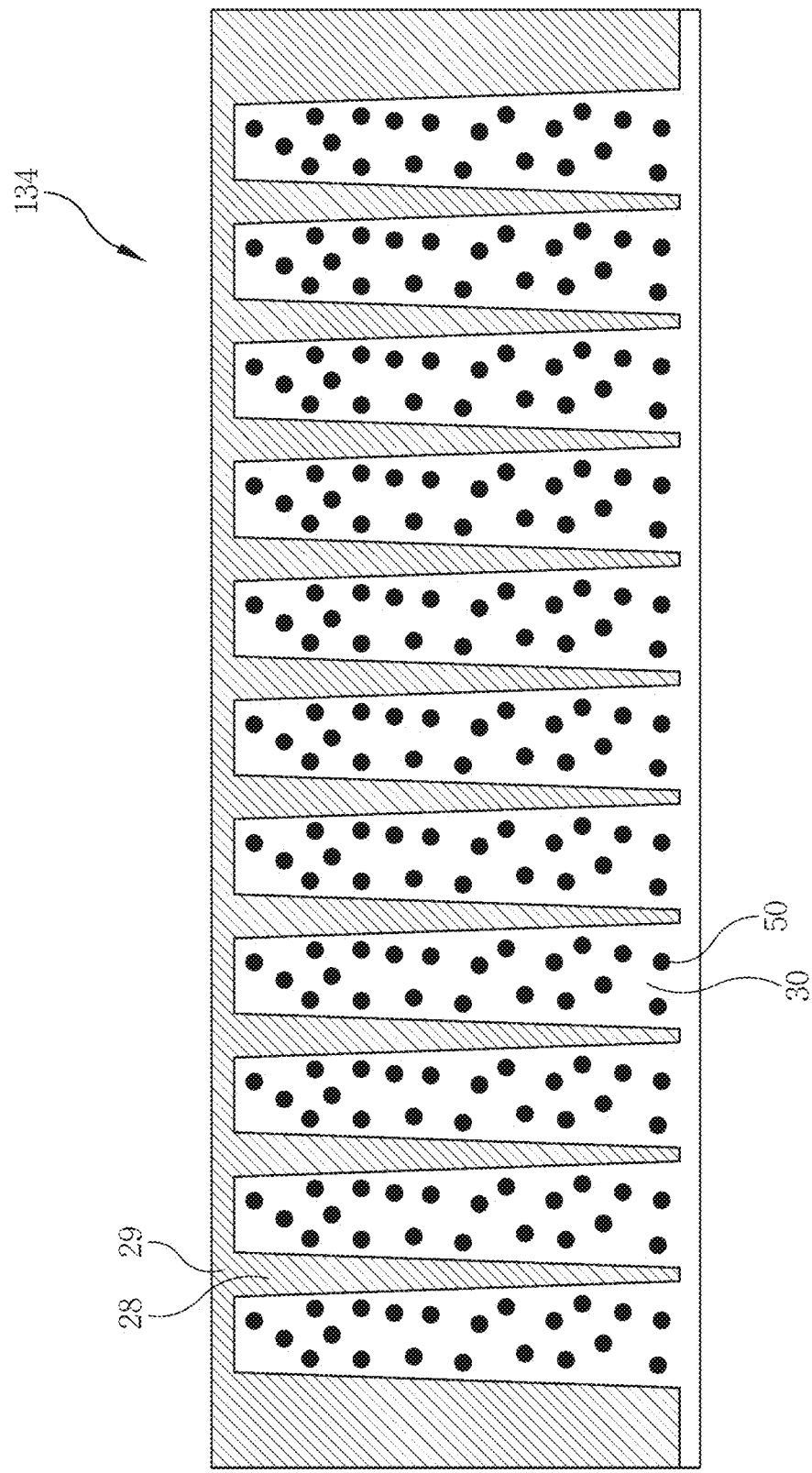

[FIG. 17]
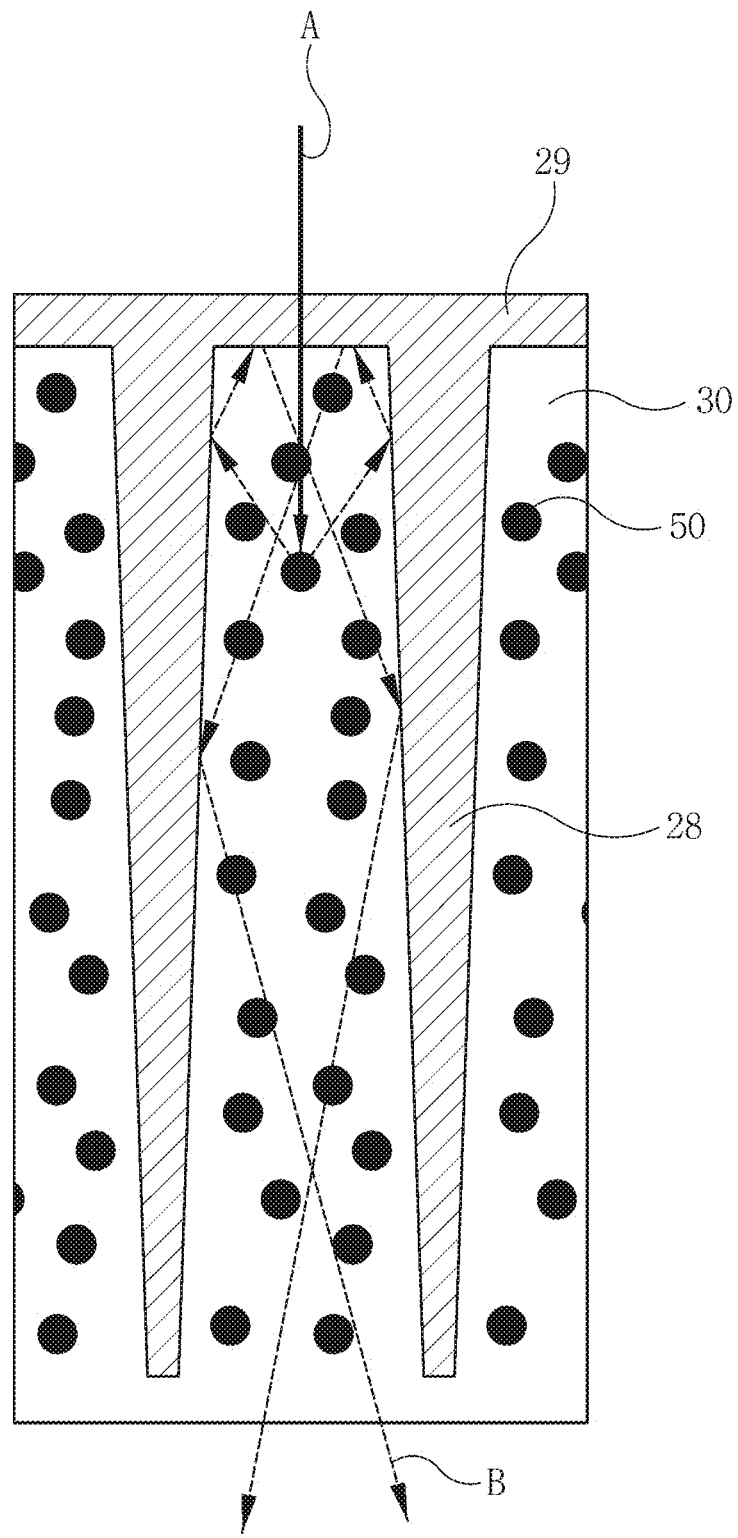

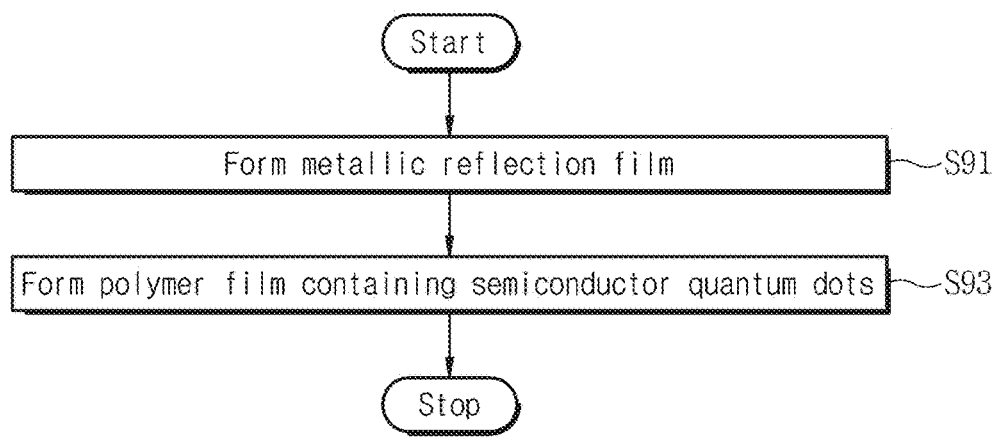
[FIG. 18]

SCINTILLATOR USING SEMICONDUCTOR QUANTUM DOTS, MANUFACTURING METHOD THEREOF, AND DIGITAL IMAGE DIAGNOSTIC SYSTEM EMPLOYING THE SAME

CROSS-REFERENCE TO RELATED APPLICATION

This application claims the benefit of Korean Patent Application No. 10-2017-0066148, filed on May 29, 2017, in the Korean Intellectual Property Office, the disclosure of which is incorporated herein in its entirety by reference.

BACKGROUND

1. Field

The present disclosure relates to a device for converting an X-ray into visible light and a digital image diagnostics system employing the device. More particularly, the present disclosure relates to a scintillator that can exhibit enhanced resolution and shortened decay time. Additionally, the present disclosure relates to a method of manufacturing the scintillator and a digital image diagnostic system employing the scintillator.

2. Description of the Related Art

Generally, digital image diagnostic systems such as an X-ray apparatus may be divided into two categories: a direct conversion type system and an indirect conversion type system.

The direct conversion type diagnostic system directly converts an incident X-ray into an electrical signal by use of a photoconductor and generates a diagnostic image using the electrical signal. Contrarily, the indirect conversion type diagnostic system converts the incident X-ray from into visible light by use of a scintillator, converts the visible light into an electrical signal by use of a photodiode, and then generates a diagnostic image using the electrical signal. One example of the indirect conversion type diagnostic system is disclosed in a Korean non-examined patent publication No. 2014-0050305 entitled COMBINATION TYPE SCINTILLATOR PANEL AND MANUFACTURING METHOD THEREOF.

In the direct conversion type diagnostic system, an increased thickness for enhancing an absorption ratio of the X-ray does not cause a decrease in a resolution of the system since the incident X-ray is instantaneously converted into electron-hole pairs and exits the photoconductor under a bias voltage. In the indirect conversion type diagnostic system, however, when the X-ray is converted into the visible light in the scintillator, the resolution of the system be lowered due to spreading of the visible light. Therefore, needed are a scintillator having a structure capable of limiting an optical path in a direction toward the photodiode in the indirect conversion type diagnostic system, and process technologies for manufacturing the scintillator.

SUMMARY

Provided are a scintillator using semiconductor quantum dots that may exhibit enhanced resolution and shortened decay time, a method of manufacturing the scintillator, and a digital image diagnostic system employing the scintillator.

Additional aspects will be set forth in part in the description which follows and, in part, will be apparent from the description, or may be learned by practice of the presented exemplary embodiments.

According to an aspect of an exemplary embodiment, a scintillator using semiconductor quantum dots, includes: a metallic reflection film made of a metal capable of transmitting an X-ray and reflecting visible light and having a plurality of voids formed in a thickness direction; a polymer film formed inside the plurality of voids and being configured to include a plurality of columnar structures to convert the X-ray into the visible light; and semiconductor quantum dots dispersed in the polymer film and having a decay time of tens of nanoseconds.

The scintillator may further include an auxiliary metallic reflection film formed of the metal to block one end of the metallic reflection film corresponding to a direction in which the X-ray is incident so as to guide a travelling direction of the visible light after reflections inside the plurality of voids in the metallic reflection film.

A sectional dimension of each of the plurality of voids may be getting larger from an end where the X-ray is incident toward an opposite direction.

The semiconductor quantum dots may be made of a semiconductor material containing at least one element selected from an elements group consisting of: cadmium, mercury, lead, and tellurium.

According to an aspect of another exemplary embodiment, a digital image diagnostic system includes: an X-ray tube configured to generate an X-ray; a scintillator configured to convert the X-ray generated by the X-ray tube into visible light; a photodiode configured to convert the visible light from the scintillator into an electrical signal; a controller configured to generate a diagnostic image by using the electrical signal output by the photodiode; and an output unit configured to output the diagnostic image generated by the controller. The scintillator includes: a metallic reflection film made of a metal capable of transmitting the X-ray and reflecting the visible light and having a plurality of voids formed in a thickness direction; a polymer film formed inside the plurality of voids and being configured to include a plurality of columnar structures to convert the X-ray into the visible light; and semiconductor quantum dots dispersed in the polymer film and having a decay time of tens of nanoseconds.

According to an aspect of yet another exemplary embodiment, a method of manufacturing a scintillator includes: forming a metallic reflection film made of a metal capable of transmitting an X-ray and reflecting visible light and having a plurality of voids formed in a thickness direction, and an auxiliary metallic reflection film made of the metal to block one end of the metallic reflection film corresponding to a direction in which the X-ray is incident so as to guide a travelling direction of the visible light after reflections inside the plurality of voids; and forming a polymer film having a plurality of columnar structures by immersing the metallic reflection film into a polymer liquid in which semiconductor quantum dots having a decay time of tens of nanoseconds are dispersed so that the polymer liquid permeates into the plurality of voids or by pouring the polymer liquid on the metallic reflection film.

The operation of forming the metallic reflection film and the auxiliary metallic reflection film may include an operation of: forming the plurality of voids while controlling depths of the plurality of voids so that the auxiliary metallic reflection film is formed at one side of the plurality of voids.

The operation of forming the metallic reflection film and the auxiliary metallic reflection film may include an operation of: performing a photolithography process and an etching process on the metal such that a sectional dimension of each of the plurality of voids is getting larger from an end where the X-ray is incident toward an opposite direction.

The operation of forming the metallic reflection film and the auxiliary metallic reflection film may include operations of: preparing a substrate; coating a photosensitive polymer material on the substrate; performing a photolithography process to form the plurality of voids in the polymer material; coating the metal on the polymer material in which the plurality of voids are formed; and removing the substrate.

The operation of forming the metallic reflection film and the auxiliary metallic reflection film may include operations of: preparing a substrate; depositing the metal on the substrate; performing a photolithography process and an etching process on the metal to form the plurality of voids in the metal; and removing the substrate.

The operation of forming the polymer film may include an operations of: annealing the polymer liquid after the plurality of voids are filled with the polymer liquid.

The scintillator according to the present disclosure includes the metallic reflection film made of a material capable of reflecting the visible light and a polymer film containing the semiconductor quantum dots having a short decay time of several tens of nanoseconds as described above. Thus, the scintillator and the digital image diagnostic system employing the scintillator may enhance a resolution of the diagnostic image and shorten the decay time, so as to enable real-time imaging and facilitate rapid analysis of the image.

BRIEF DESCRIPTION OF THE DRAWINGS

These and/or other aspects will become apparent and more readily appreciated from the following description of the exemplary embodiments, taken in conjunction with the accompanying drawings.

FIG. 1 is a block diagram of a digital image diagnostic system including a scintillator according to an embodiment of the present disclosure.

FIG. 2 is a perspective view of the scintillator shown in FIG. 1.

FIGS. 3 through 5 illustrate a process of fabricating the scintillator of FIG. 2.

FIG. 6 illustrates a first embodiment of fabricating the metallic reflection film shown in FIG. 3.

FIG. 7 illustrates a second embodiment of fabricating the metallic reflection film shown in FIG. 3.

FIG. 8 illustrates a third embodiment of fabricating the metallic reflection film shown in FIG. 3.

FIG. 9 illustrates a fourth embodiment of fabricating the metallic reflection film shown in FIG. 3.

FIG. 10 is a vertical cross-sectional view of a scintillator according to a first embodiment of the present disclosure.

FIG. 11 is a diagram for explaining a process of converting an X-ray into visible light and emitting the visible light in the scintillator of FIG. 10.

FIG. 12 is a vertical cross-sectional view of a scintillator according to a second embodiment of the present disclosure.

FIG. 13 is a diagram for explaining a process of converting an X-ray into visible light and emitting the visible light in the scintillator of FIG. 12.

FIG. 14 is a vertical cross-sectional view of a scintillator according to a third embodiment of the present disclosure.

FIG. 15 is a diagram for explaining a process of converting an X-ray into visible light and emitting the visible light in the scintillator of FIG. 14.

FIG. 16 is a vertical cross-sectional view of a scintillator according to a fourth embodiment of the present disclosure.

FIG. 17 is a diagram for explaining a process of converting an X-ray into visible light and emitting the visible light in the scintillator of FIG. 16.

FIG. 18 is a flowchart illustrating a method of manufacturing a scintillator according to an embodiment of the present disclosure.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects.

FIG. 1 is a block diagram of a digital image diagnostic system including a scintillator according to an embodiment of the present disclosure.

A digital image diagnosis system 100 shown in FIG. 1, which is an indirect conversion type diagnostic system, may improve the image resolution and shorten a decay time so as to facilitate real-time imaging and rapid analysis of the image. The digital imaging system 100 may include an X-ray tube 110, a scintillator 130, a photodiode 150, a controller 170, and an output unit 190.

The X-ray tube 110 is formed as a vacuum tube and generates an X-ray. The X-ray tube 110 generates an electron beam moving at high speeds and colliding with another substance to generate the X-ray. The X-ray tube 110 may be categorized into a hot cathode X-ray tube and a gas-filled X-ray tube according to a mechanism of generating the X-ray.

The scintillator 130 may converts the X-ray generated by the X-ray tube 110 and transmitted through a human body being diagnosed into the visible light. The scintillator 130 may exhibit an increased reflectance or reflection ratio by using a metallic reflection film made of a material capable of reflecting visible light and a polymer film containing semiconductor quantum dots. Here, the semiconductor quantum dots are formed to be dispersed in the polymer film and have decay times of several tens of nanoseconds. In addition, the semiconductor quantum dots may have an X-ray extinction effect. Thus, the scintillator 130 may reveal an increased efficiency of converting the X-rays into visible light, minimize spreading of the visible light, and emit the visible light of a high intensity toward the photodiode 150.

The photodiode 150 converts the light energy of the visible light beam from the scintillator 130 into an electrical signal by generating electron-hole pairs and a resultant current proportional to the intensity of the visible light when the visible light is incident on its light receiving surface. Thus, the photodiode 150 may convert the light energy into the electrical signal having a voltage enough to be detected.

The controller 170 may detect an image represented by the electrical signal output by the photodiode 150. That is, the controller 170 may generate a diagnostic image by detecting digitizing the electrical signal from the photodiode 150. In addition, the controller 170 may photograph and analyze a video image in real time as the decay time is shortened.

The output unit 190 outputs the diagnostic image generated by the controller 170. The output unit 190 may include a monitor, a projector, a printer, and the like to allow the user to check the image.

FIG. 2 is a perspective view of the scintillator shown in FIG. 1, and FIGS. 3 through 5 illustrate a process of fabricating the scintillator of FIG. 2.

Referring to FIGS. 2 through 5, the scintillator 130 may include a metallic reflection film 10, a polymer film 30, and semiconductor quantum dots 50.

The metallic reflection film 10 is made of metal transmitting an X-ray and but reflecting visible light. A plurality of voids are formed in a thickness direction in the metallic reflection film 10. The plurality of voids may have a polygonal or circular cross-section and be arranged periodically. The metallic material used for the metallic reflection film 10 may exhibit high reflectance in a visible light range. Examples of the metallic material may include silver (Ag), aluminum (Al), or the like.

The polymer film 30 contains the semiconductor quantum dots 50 and converts an incident X-ray into the visible light by the semiconductor quantum dots 50. The polymer film 30 is disposed inside the plurality of voids in the metallic reflection film 10, and forms a plurality of columnar structures. The polymer film 30 may improve a spatial resolution due to the plurality of columnar structures. Here, the plurality of columnar structures may be micro-columnar structures.

The semiconductor quantum dots 50 are dispersed in the polymer film 30 and may have a decay time of several tens of nanoseconds. The semiconductor quantum dots 50 may show an X-ray extinction effect. Since emission wavelengths of the semiconductor quantum dots 50 vary according to dimensions of the quantum dots, the emission wavelengths of the semiconductor quantum dots 50 may be adjusted easily. Also, the semiconductor quantum dots 50 are advantageous for a spectral matching with the photodiode 150 due to a narrow half width in a frequency distribution curve. The semiconductor quantum dots 50 may be fabricated using semiconductor materials such as cadmium sulfide (CdS), cadmium selenide (CdSe), and cadmium telluride (CdTe). Preferably, the semiconductor materials used for fabricating the semiconductor quantum dots 50 may include at least one element among cadmium (Cd), mercury (Hg), lead (Pb), and tellurium (Te).

The scintillator 130 may be fabricated by a following process.

First, the metallic reflection film 10 is formed. The metallic reflection film 10 is made of the metal capable of transmitting the X-ray and reflecting the visible light and is formed to include the plurality of voids in the thickness direction. Then the metallic reflection film 10 is immersed into a polymer liquid 31, which contains the semiconductor quantum dots 50. As a result, the polymer liquid 31 permeates into the plurality of voids in the metallic reflection film 10. Afterwards, the metallic reflection film 10 into which the polymer liquid 31 permeated is subjected to an annealing, so that the polymer liquid 31 is hardened to become the polymer film 30. Thus, the fabrication of the scintillator 130 is completed.

Though the process of immersing the metallic reflection film 10 into the polymer liquid 31 is exemplarily illustrated in the drawing, the present disclosure is not limited thereto and the polymer liquid 31 may be introduced into the plurality of voids in the metallic reflection film 10 by pouring over the plurality of voids in the metallic reflection film 10.

FIG. 6 illustrates a first embodiment of fabricating the metallic reflection film shown in FIG. 3.

Referring to FIG. 6, the metallic reflection film 10 according to the first embodiment (Hereinbelow, referred to as 'first metallic reflection film') may be formed by coating a metal on a porous structure 15 formed of a polymer.

In more detail, the first metallic reflection film may be formed as follows. A substrate 11 is prepared first. Subsequently, a polymer material 13 is coated on the substrate 11. The substrate 11 may be selected from a variety of substrates such as a silicon substrate and a glass substrate. The polymer material 13 may be a photosensitive polymer material such as a photoresist (PR).

Subsequently, a porous structure 15 having a plurality of voids 14 is formed by performing a photolithographic process on the polymer material 13 coated on the substrate 11. At this time, the photolithographic process is performed for the polymer material 13 disposed on the substrate 11 to the extent that the substrate 11 is revealed, so that the plurality of voids 14 are formed. Thus, the porous structure 15 becomes a shape in which the plurality of voids 14 or through-cuts would pass through the porous structure 15 when the substrate 11 is removed in the future.

Afterwards, the porous structure 15 is coated with the metal capable of transmitting the X-ray and reflecting the visible light to form a columnar metallic reflection film 17. At this time, the metal may be coated by various processes such as thermal evaporation, electron beam evaporation, radio frequency or direct current (RF/DC) sputtering, solution coating, silver halide reaction, and the like.

Finally, the substrate 11 is removed to form the first metallic reflection film 10 in which the porous structure 15 formed of the polymer is coated with the metal.

FIG. 7 illustrates a second embodiment of fabricating the metallic reflection film shown in FIG. 3.

Referring to FIG. 7, the metallic reflection film 10 according to the second embodiment (Hereinbelow, referred to as 'second metallic reflection film') may be formed by coating the metal on a porous structure 15 formed of a polymer and an auxiliary structure 16.

The second metallic reflection film 10 may be formed by a process similar to the process for the first metallic reflection film 10 described above. However, there is a difference in the process of forming the plurality of voids 14 by performing the photolithographic process on the polymer material 13 coated on the substrate 11.

That is, contrary to the first metallic reflection film 10 in which the photolithographic process is performed to the extent that the substrate 11 is revealed and the voids 14 are formed in forms of the through-cuts, the photolithographic process is performed in the present embodiment to the extent that some portion of the polymer material 13 disposed on the substrate 11 of a predetermined thickness is remained to form the auxiliary structure 16. Accordingly, the porous structure 15 will a shape that one side of the voids 14 corresponding to a direction in which the X-ray is incident is blocked by the auxiliary structure 16 when the substrate 11 is removed in the future.

Afterwards, the porous structure 15 and the auxiliary structure 16 are coated with the metal capable of transmitting the X-ray and reflecting the visible light to form a metallic reflection film including a columnar metallic reflection film 17 and the auxiliary metallic reflection film 19, respectively.

Finally, the substrate 11 is removed to complete the second metallic reflection film 10 in which the porous structure 15 and the auxiliary structure 16 both being formed of the polymer are coated with the metallic reflection film.

FIG. 8 illustrates a third embodiment of fabricating the metallic reflection film shown in FIG. 3.

Referring to FIG. 8, the metallic reflection film 10 according to the third embodiment (Hereinbelow, referred to as 'third metallic reflection film') may be formed by performing the photolithographic process and an etching process on a metallic film.

In more detail, the first metallic reflection film may be formed as follows. A substrate 11 is prepared first. Subsequently, a metal is coated on the substrate 21 to form the metallic film 23. Here, the metal may have a property of transmitting the X-ray and reflecting the visible light and may exhibit high reflectance in the visible light range. The metal may be coated by various processes such as thermal evaporation, the electron beam evaporation, the RF/DC sputtering, the solution coating, the silver halide reaction, and the like.

Subsequently, a plurality of voids 24 are formed by performing the photolithographic process and the etching process on the metallic film 23 disposed on the substrate 21. At this time, the photolithographic process and the etching process are performed to the extent that the substrate 21 is revealed. Thus, the plurality of voids 24 are formed as the through-cuts passing through the metallic film 23 when the substrate 21 is removed in the future.

Finally, the substrate 21 is removed to form the second metallic reflection film 10 having a columnar metallic reflection film 27.

FIG. 9 illustrates a fourth embodiment of fabricating the metallic reflection film shown in FIG. 3.

Referring to FIG. 9, the metallic reflection film 10 according to the fourth embodiment (Hereinbelow, referred to as 'fourth metallic reflection film') may be formed by performing the photolithographic process and the etching process on a metallic film.

The fourth metallic reflection film 10 may be formed by a process similar to the process for the third metallic reflection film 10 described above. However, there is a difference in the process of forming the plurality of voids 24 by performing the photolithographic process and the etching process on the polymer material 13 on the metallic film coated on the substrate 21.

That is, contrary to the third metallic reflection film 10 in which the photolithographic process and the etching process are performed to the extent that the substrate 21 is revealed and the voids 24 are formed in forms of the through-cuts, the photolithographic process and the etching process are performed in the present embodiment to the extent that some portion of the metallic film 23 coated on the substrate 21 of a predetermined thickness is remained to form an auxiliary metallic reflection film 29. Accordingly, the columnar metallic reflection film 27 will a shape that one side of the voids 24 corresponding to a direction in which the X-ray is incident is blocked by the auxiliary metallic reflection film 29 when the substrate 21 is removed in the future.

FIG. 10 is a vertical cross-sectional view of a scintillator according to a first embodiment of the present disclosure, and FIG. 11 illustrates a process that the scintillator of FIG. 10 converts an X-ray into visible light and emit the visible light.

Referring to FIGS. 10 and 11, a scintillator 131 according to a first embodiment (hereinbelow, referred to as 'first scintillator') includes a columnar metallic reflection film 27 and a polymer film 30. The polymer film 30 contains the semiconductor quantum dots 50 having a decay time of tens of nanoseconds.

The first scintillator 131 may convert the X-ray (A) into the visible light (B). Here, the first scintillator 131 may exhibit a high resolution, after the X-ray (A) is converted into the visible light (B), owing to the columnar metallic reflection film 27 which is disposed vertically in the drawing to confine consecutively-reflected visible lights in a small region. In particular, the semiconductor quantum dots 50 contained in the polymer film 30 may reduce the decay time so as to enable a shooting of a high-speed moving picture.

However, the first scintillator 131 may be disadvantageous in that the visible light (B) is emitted in both upward and downward directions in the drawing, which may result in a considerable spreading of the visible light or a loss of the visible light energy.

FIG. 12 is a vertical cross-sectional view of a scintillator according to a second embodiment of the present disclosure, and FIG. 13 illustrates a process that the scintillator of FIG. 12 converts an X-ray into visible light and emit the visible light.

A scintillator 132 according to the second embodiment (hereinbelow, referred to as 'second scintillator') shown in FIGS. 12 and 13 is configured to reduce the visible light spreading phenomenon of the first scintillator 131.

The columnar metallic reflection film 27 of the second scintillator 132 has a sectional shape different from that of the first scintillator 131. In more detail, contrary to the columnar metallic reflection film 27 of the first scintillator 131 which has a rectangular cross section, for example, having a pair of parallel sides, the columnar metallic reflection film 27 of the second scintillator 132 has a tapered cross section in which the thickness of the columnar metallic reflection film 27 becomes narrower from the upper portion to the lower portion. Accordingly, in the second scintillator 132, a sectional dimension of each void (i.e., a gap between adjacent two gratings of the columnar metallic reflection film 27 in the drawing) is larger at a bottom end than at a top end, and a more quantity of the polymer film 30 is filled at a lower portion than at a upper portion.

Due to such an asymmetric structure in the upward and downward directions, a larger portion of the visible light may be emitted in the downward direction than in upward direction after consecutive reflections at walls of the columnar metallic reflection film 27 and the semiconductor quantum dots 50. Thus, the visible light spreading or the loss of light energy arising from the exit of the light in the upward direction may be reduced. Here, the downward direction is the direction facing the photodiode 150 of FIG. 1.

FIG. 14 is a vertical cross-sectional view of a scintillator according to a third embodiment of the present disclosure, and FIG. 15 illustrates a process that the scintillator of FIG. 14 converts an X-ray into visible light and emit the visible light.

A scintillator 133 according to the third embodiment (hereinbelow, referred to as 'third scintillator') shown in FIGS. 14 and 15 is configured to reduce the visible light spreading phenomenon of the first scintillator 131.

In detail, the third scintillator 133 has a structure that the auxiliary metallic reflection film 29 is added to a up side of the voids 24 in the columnar metallic reflection film 27 corresponding to a direction in which the X-ray is incident, so that the up side of the voids 24 in the columnar metallic reflection film 27 are blocked by the auxiliary metallic reflection film 29. Due to the auxiliary metallic reflection film 29, the third scintillator 133 may enhance a directivity of the visible light and reduce the visible light spreading phenomenon.

FIG. 16 is a vertical cross-sectional view of a scintillator according to a fourth embodiment of the present disclosure, and FIG. 17 illustrates a process that the scintillator of FIG. 16 converts an X-ray into visible light and emit the visible light.

A scintillator 134 according to the fourth embodiment (hereinbelow, referred to as 'fourth scintillator') shown in FIGS. 16 and 17 is configured to employ the features of both the second scintillator 132 and the third scintillator 133 to reduce the visible light spreading phenomenon of the first scintillator 131.

In detail, the fourth scintillator 134 is configured to include the features of a modified shape of the columnar metallic reflection film 28 in the second scintillator 132 and the addition of the auxiliary metallic reflection film 29 in the third scintillator 133. Owing to such a configuration, the fourth scintillator 134 may reduce the visible light spreading or the loss of the visible light energy and enhance the directivity of the visible light, such that no visible light exits in the upward direction and all the visible light is emitted in the downward direction. Thus, the fourth scintillator 134 may exhibit a higher light conversion efficiency than the first through third scintillators 131-133.

FIG. 18 is a flowchart illustrating a method of manufacturing a scintillator according to an embodiment of the present disclosure.

Referring to FIGS. 2 and 18, the scintillator 130 may include the metallic reflection film 10 and the polymer film 30 which contains the semiconductor quantum dots 50.

In operation S91, a metallic reflection film 10 is formed. The metallic reflection film 10 is formed of a metal capable of transmitting the X-ray and reflecting the visible light. The metallic reflection film 10 may includes a plurality of voids in the thickness direction. Here, examples of the metal may include silver, aluminum, or the like. The metallic reflection film 10 may be formed by coating the metal on a porous structure formed of the polymer or by depositing the metal film and performing the photolithography process and the etching process on the metal film.

In operation S93, the polymer film 30 containing the semiconductor quantum dots 50 is formed. The polymer film 30 may be formed by immersing the metallic reflection film 10 in the polymer liquid in which the semiconductor quantum dots 50 are dispersed or by pouring the polymer liquid on the metallic reflection film 10 and then performing the annealing process. In other words, the polymer film 30 may be formed by introducing the polymer liquid into the voids formed in the metallic reflection film 10 and hardening the polymer through the annealing process. Preferably, the polymer liquid helps semiconductor quantum dots 50 to maintain a state of being dispersed, thereby preventing the semiconductor quantum dots 50 from aggregating in one region in the polymer film 30.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A scintillator using semiconductor quantum dots, comprising:
   a metallic reflection film made of a metal, wherein the metallic reflection film is transmissive to an X-ray and reflective to a visible light, wherein the metallic reflection film comprises a plurality of voids formed in a thickness direction;
   a polymer film comprising a plurality of columnar structures formed inside the plurality of voids of the metallic reflection film; and
   semiconductor quantum dots dispersed in the plurality of columnar structures of the polymer film, the semiconductor quantum dots being configured to convert the X-ray into the visible light and having a decay time of tens of nanoseconds.

2. The scintillator according to claim 1, further comprising:
   an auxiliary metallic reflection film formed of the metal to block one end of the metallic reflection film corresponding to a direction in which the X-ray is incident so as to guide a travelling direction of the visible light after reflections inside the plurality of voids in the metallic reflection film.

3. The scintillator according to claim 1, wherein a sectional dimension of each of the plurality of voids is getting larger from an end where the X-ray is incident toward an opposite direction.

4. The scintillator according to claim 1, wherein the semiconductor quantum dots is made of a semiconductor material containing at least one element selected from a group consisting of: cadmium, mercury, lead, and tellurium.

5. A digital image diagnostic system, comprising:
   an X-ray tube configured to generate an X-ray;
   a scintillator configured to convert the X-ray generated by the X-ray tube into visible light;
   a photodiode configured to convert the visible light from the scintillator into an electrical signal;
   a controller configured to generate a diagnostic image by using the electrical signal output by the photodiode; and
   an output unit configured to output the diagnostic image generated by the controller,
   wherein the scintillator comprises:
      a metallic reflection film made of a metal, the metallic reflection film being transmissive to an X-ray and reflective to a visible light, the metallic reflection film comprising a plurality of voids formed in a thickness direction;
      a polymer film comprising a plurality of columnar structures formed inside the plurality of voids of the metallic reflection film; and
      semiconductor quantum dots dispersed in the plurality of columnar structures of the polymer film, the semiconductor quantum dots being configured to convert the X-ray into the visible light and having a decay time of tens of nanoseconds.

6. A method of manufacturing a scintillator, comprising:
   forming a metallic reflection film made of a metal, the metallic reflection film being transmissive to an X-ray and reflective to a visible light, the metallic reflection film comprising a plurality of voids formed in a thickness direction, and
   forming an auxiliary metallic reflection film made of the metal to block one end of the metallic reflection film corresponding to a direction in which the X-ray is incident so as to guide a travelling direction of the visible light after reflections inside the plurality of voids; and forming a polymer film having a plurality of columnar structures formed inside the plurality of voids of the metallic reflection film by immersing the metallic reflection film into a polymer liquid in which semiconductor quantum dots having a decay time of tens of nanoseconds are dispersed or by pouring the polymer liquid on the metallic reflection film such that the semiconductor quantum dots are dispersed inside the plurality of columnar structures.

7. The method as claimed in claim 6, wherein the operation of forming the metallic reflection film and the auxiliary metallic reflection film comprises:

forming the plurality of voids while controlling depths of the plurality of voids so that the auxiliary metallic reflection film is formed at one side of the plurality of voids.

8. The method as claimed in claim 6, wherein the operation of forming the metallic reflection film and the auxiliary metallic reflection film comprises:

performing a photolithography process and an etching process on the metal such that a sectional dimension of each of the plurality of voids is getting larger from an end where the X-ray is incident toward an opposite direction.

9. The method as claimed in claim 6, wherein the operation of forming the metallic reflection film and the auxiliary metallic reflection film comprises:

preparing a substrate;

coating a photosensitive polymer material on the substrate;

performing a photolithography process to form the plurality of voids in the polymer material;

coating the metal on the polymer material in which the plurality of voids are formed; and removing the substrate.

10. The method as claimed in claim 6, wherein the operation of forming the metallic reflection film and the auxiliary metallic reflection film comprises:

preparing a substrate;

depositing the metal on the substrate;

performing a photolithography process and an etching process on the metal to form the plurality of voids in the metal; and removing the substrate.

11. The method as claimed in claim 6, wherein the operation of forming the polymer film comprises:

annealing the polymer liquid after the plurality of voids are filled with the polymer liquid.

* * * * *